United States Patent
Drube

(10) Patent No.: US 6,770,635 B1
(45) Date of Patent: Aug. 3, 2004

(54) METHOD FOR MEDICATING THE INFLAMMATORY CONTROLLING SYSTEM AND ADVERSE INFLAMMATORY REACTIONS AND FOR MAKING COMPOUNDS FOR TREATING THE PATHOLOGY OF ADVERSE INFLAMMATORY REACTIONS

(75) Inventor: Clairmont G. Drube, Green Valley, AZ (US)

(73) Assignee: Pharos Pharmaceuticals, Rochester, NY (US)

( * ) Notice: Subject to any disclaimer, the term of this patent is extended or adjusted under 35 U.S.C. 154(b) by 0 days.

(21) Appl. No.: 08/984,947

(22) Filed: Dec. 4, 1997

Related U.S. Application Data

(63) Continuation of application No. PCT/US96/08599, filed on Jun. 6, 1996, which is a continuation-in-part of application No. 08/470,501, filed on Jun. 6, 1995, now Pat. No. 5,631,245.

(51) Int. Cl.$^7$ .............................................. A61K 31/70
(52) U.S. Cl. ......................... 514/62; 514/814; 514/826; 514/860; 514/861; 514/863; 514/866; 514/884; 514/885; 514/886; 514/893; 514/912; 514/931; 514/934; 536/18.7; 536/22.1; 536/53
(58) Field of Search .......................... 514/62, 814, 826, 514/860, 861, 863, 866, 884, 885, 886, 893, 912, 931, 934; 536/18.7, 22.1, 53

(56) References Cited

U.S. PATENT DOCUMENTS

| | | | |
|---|---|---|---|
| 4,647,453 A | | 3/1987 | Meisner |
| 4,695,590 A | | 9/1987 | Lippman |
| 4,737,488 A | | 4/1988 | Lockhoff et al. |
| 4,772,591 A | | 9/1988 | Meisner |
| 4,870,061 A | | 9/1989 | Speck |
| 4,957,906 A | | 9/1990 | Yoshikumi et al. |
| 5,160,742 A | * | 11/1992 | Mazer et al. |
| 5,177,062 A | | 1/1993 | Miyata et al. |
| 5,219,843 A | | 6/1993 | Macher |
| 5,248,668 A | | 9/1993 | Wu |
| 5,362,480 A | * | 11/1994 | Au et al. ....................... 424/54 |
| 5,631,245 A | * | 5/1997 | Drube .......................... 514/62 |
| 5,872,111 A | * | 2/1999 | Au et al. ...................... 514/62 |

FOREIGN PATENT DOCUMENTS

| | | |
|---|---|---|
| DE | A 3347522 | 7/1985 |
| WO | 96/39153 | 12/1996 |

OTHER PUBLICATIONS

Panigot et al., "Reaction of Glycosyl Halides with Benzyl Grignard Reagents: Unexpected o–Tolyl . . . ", *J. Carbohydrate Chemistry*, vol. 13, No. 2, 1994, pp. 293–302.
Tsuchida et al., "Formation of Deoxy–fructosazine . . . ", *Agr. Biol. Chem.*, vol. 37, No. 11, 1973, pp. 2571–2578.
Linek et al., "Structure and Rearrangement Reactions . . . ", *Carbohydrate Research*, vol. 164, 1987, pp. 195–205.
Hodge et al., "Preparation and Properties of Dialditylamines", vol. 28, Oct., 1963, pp. 2784–2788.
Pigman, Horton, EDS.: "The Carbohydrates", 1980, Academic Press, New York, p. 882 especially, see pp. 881–927. XP002024381 113900.
Carbohyde. Res., vol. 273, No. 1, 1995, pp. 109–113, XP0000604637 N. Kolarva et al.: "Inhibitory effect of diglycosylamines on two betoglucosidases".

* cited by examiner

*Primary Examiner*—James O. Wilson
*Assistant Examiner*—Patrick Lewis
(74) *Attorney, Agent, or Firm*—Shoemaker and Mattare LTD; Charles W. Fallow

(57) ABSTRACT

Adverse inflammatory reactions can be treated by administrating to an organism a composition having diglucosylamine as the active ingredient. The preferred compound is di-Beta-D-glucopyranosylamine. A simple method for making diglucosylamine in high purity is obtained by reacting glucose, a nitrogen containing base, and either methanol or ethanol to form the diglucosylamine and then recovering the diglucosylamine preferably with the use of charcoal. The preferred diglucosylamine, di-Beta-D-glucopyranosylamine, has extraordinary anti-inflammatory activity. It can be formulated with a pharmaceutically acceptable carrier to make pharmaceutical compositions which are effective in treating inflammations. This pharmaceutical composition can also be used to treat adverse inflammatory reactions that are the result of the disruptions of a dynamic network of cellular mechanisms in organisms. In addition, application of this composition also serves to reestablish the balance of the cellular defense network in an organism which has its cellular defense network out of balance. In this unbalanced case, the composition serves to treat the pathology of inflammation and activates the inflammatory control system in vivo. These adverse inflammatory reactions can also be treated by administrating to the organism glucose in the presence of $NH_3^+$ ions and at a pH of about 7.0 or greater. The glucose can preferably be applied by orally administrating an enteric-coated form of glucose, alone or in combination with other medicaments.

11 Claims, 1 Drawing Sheet

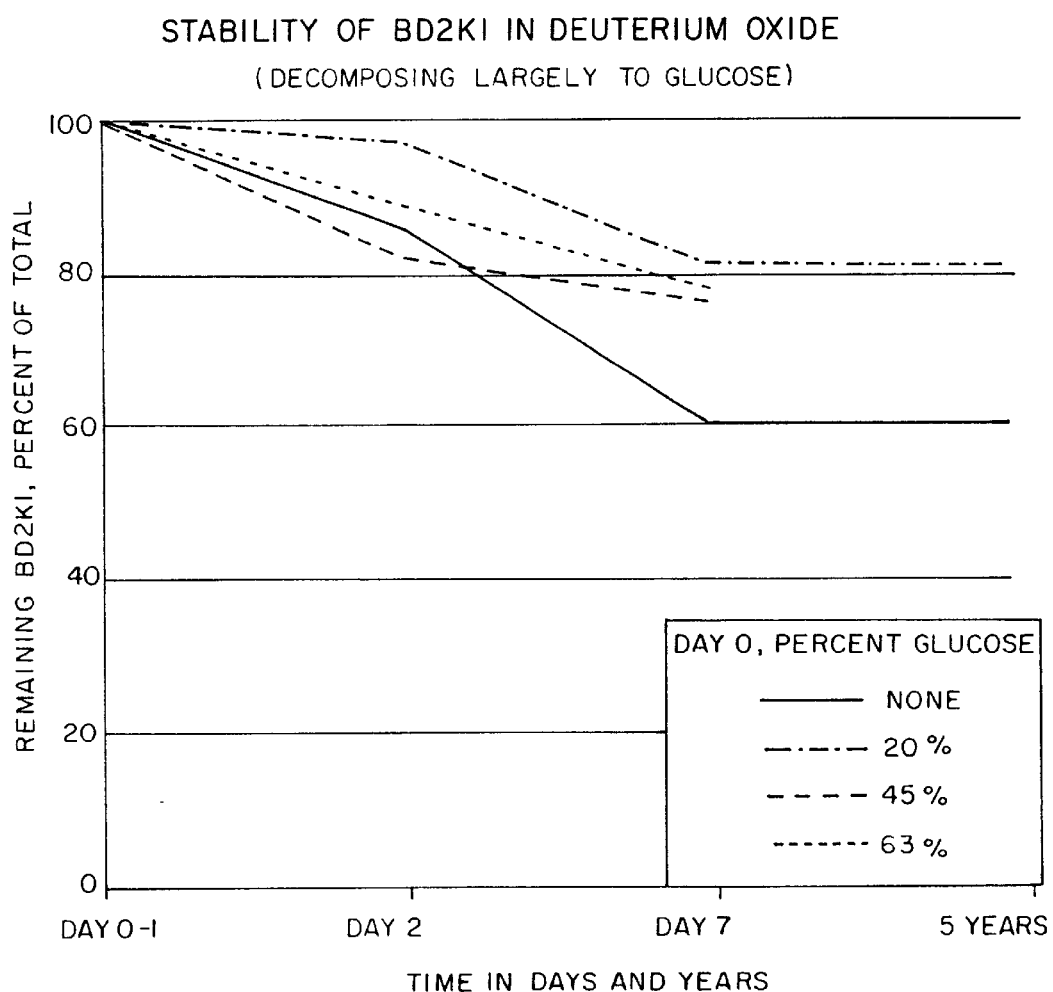

METHOD FOR MEDICATING THE INFLAMMATORY CONTROLLING SYSTEM AND ADVERSE INFLAMMATORY REACTIONS AND FOR MAKING COMPOUNDS FOR TREATING THE PATHOLOGY OF ADVERSE INFLAMMATORY REACTIONS

This is a 371 of PCT/US96/08599, filed Jun. 6, 1996; which is a continuation-in-part of 08/470,501, filed Jun. 6, 1995; now U.S. Pat. No. 5,631,245, issued May 20, 1997.

BACKGROUND OF THE INVENTION

1. Field of the Invention

This invention relates to the use of di-Beta-D-glucopyranosylamine compounds for controlling the inflammatory controlling system and related diseases and to methods for making the compounds.

2. Description of the Previously Published Art

K. Linek et al, in Carbohydrate Research, 164 (1987), pp. 195–205, discuss "Structure and Rearrangement Reactions of Some Diglycosylamines". These glycosylamines are compounds of interest for the enzymology of carbohydrates, since they are considered as active-site-directed, reversible inhibitors of glycosidases. The compound di-Beta-D-glucopyranosylamine was prepared by the transglycosylation from Beta-D-glucopyranosylamine.

This compound has been discovered in my research conducted on Transfer Factors. For a discussion of Transfer Factors, see G. B. Olson and C. G. Drube, "Modulation of Influenza in Mice by Transfer Factor Therapy" in *Journal of Reticuloendothelial Society*, Vol. 24, No. 3, Nov. 1978. The compound was obtained during purification studies on these transfer factors.

This invention is directed to simpler methods of making this compound and to the discovery of unique uses of this material for controlling the inflammatory controlling system.

3. Objects of the Invention

It is an object of this invention to provide a process for making diglucosylamine from glucose.

It is an object of this invention to provide a process for making di-Beta-D-glucopyranosylamine from glucose and especially from D-(+)-Glucose.

It is a further object of this invention to use di-Beta-D-glucopyranosylamine for controlling the inflammatory controlling system.

It is a further object of this invention to use di-Beta-D-glucopyranosylamine for treating adverse immunological reactions.

It is a further object of this invention to use di-Beta-D-glucopyranosylamine for treating adverse neurological reactions.

It is a further object of this invention to use di-Beta-D-glucopyranosylamine for treating adverse endocrine reactions.

It is a further object of this invention to use di-Beta-D-glucopyranosylamine for treating adverse direct physical or chemical injuries.

It is a further object of this invention to use di-Beta-D-glucopyranosylamine for reestablishing the balance of the cellular defense network in an organism which has its cellular defense network out of balance.

It is a further object of this invention to formulate anti-inflammatory pharmaceutical compositions containing di-Beta-D-glucopyranosylamine.

It is a further object of the invention to administer glucose to an organism in the presence of $NH_3^+$ ions and at a pH of about 7.0 or greater to treat adverse inflammatory reactions.

It is a further object of the invention to administer glucose orally in an enteric-coated form to an organism in the presence of $NH_3^+$ ions and at a pH of about 7.0 or greater to treat adverse inflammatory reactions.

These and further objects of the invention will become apparent as the description of the invention proceeds.

SUMMARY OF THE INVENTION

Adverse inflammatory reactions that are the result of the disruptions of a dynamic network of cellular mechanisms in organisms can be treated by administrating to the organism a composition having diglucosylamine as the active ingredient. The preferred compound is di-Beta-D-glucopyranosylamine. Administration of this same composition also serves to reestablish the balance of the cellular defense network in an organism which has its cellular defense network out of balance. In this case, the composition serves to treat the pathology of inflammation and activates the inflammatory control system in vivo.

A simple method for making diglucosylamine in higher purity has been developed. The method involves reacting glucose, a nitrogen containing base and either methanol or ethanol to form a diglucosylamine and then recovering the diglucosylamine preferably with the use of charcoal.

The anti-inflammatory compound di-Beta-D-glucopyranosylamine can be formulated with a pharmaceutically acceptable carrier to make pharmaceutical compositions which are effective in treating inflammations.

These adverse inflammatory reactions can also be treated by administrating to the organism glucose in the presence of $NH_3^+$ ions and at a pH of about 7.0 or greater. The glucose can preferably be applied by orally administrating an enteric-coated form of glucose, alone or in combination with other medicaments.

DESCRIPTION OF THE PREFERRED EMBODIMENTS

Diglucosylamine has been isolated from molasses and it has been synthesized from D-(+)-Glucose by two routes forming products designated BD2K1 and BD2K2. These diglucosylamines are referred to herein generally as BD2K and they have almost unbelievable anti-inflammatory powers.

In the field of anti-inflammatory agents, there are several anti-inflammatory agents designed to control specific types of inflammation based on a specific mediator of the inflammatory response. BD2K, on the other hand, acts differently because it modifies a system in vivo that directly treats all excessive types of inflammation, such as contact hypersensitivity. Therefore, the BD2K compound is broad spectrum and not a specific designed anti-inflammatory agent. Because of BD2K's broad spectrum of applications, it promises to be a good product for treating the inflammatory process and restoring to normal inflammation responses. Moreover, the product's dynamic effect lends itself to combination therapy with other drugs increasing their therapeutic index; that is, it requires less of the drug and therefore minimizes their possible toxic effects.

The very significant anti-inflammatory activity suggests that this compound will be especially useful as a part of the treatment of auto-immune diseases where part of the etiology of the disease is inflammation. The BD2K compound can be used in combination with other auto-immune diseases agents to work together to treat the disease. The BD2K compound has very good tolerance to other compounds such that they can be used together and the BD2K compound does not inhibit the activity of the other active compound.

BD2K seems to work on many levels. It is believed that BD2K repairs or supplements the genetic molecules that regulate the inflammatory control system. The inflammatory control system has a very specific biological activity in vivo. This system controls inflammation that compromises many different systems in the organisms; systems like the neurologic, digestive, metabolic, immune and endocrine. Therefore, the specific effect of BD2K on inflammation makes the compound a broad spectrum product for experimental, therapeutic and prophylactic value.

BD2K has multiple applications to most of the same symptoms as does aspirin and probably to more. However, in contrast, BD2K is very effective as a therapeutic agent applied topically without any irritation, and when it is used parentally shows no indication of toxicity. BD2K can be used in combination with other medications. The compound is a specific therapy for the dynamic positive control of inflammation. Not only does it relieve symptoms, it positively contributes to the cure of the disease, without elevating IgE levels in patient sera.

Without being bound to any particular theory or mechanism, it is postulated that the senescence and longevity of organisms depends on a balance between defense mechanisms that favor life span and the defense mechanisms that counteract disease processes. The mechanisms favoring longevity are those that cause damage to macromolecules and other body components that come from both exogenous or endogenous sources.

Ionization radiation, UV radiation, and xenobiotics, including dietary carcinogens, entailing the most common exogenous genotoxic compounds with which the organisms cope with everyday. Body heat, oxygen free radicals, glucose, and other oxidative sugars are representative of the byproducts of a variety of metabolic pathways and represent unavoidable, potentially genotoxic agents.

The endogenous hormones are involved in advanced senescence of cells or pathologies of disease in organisms. Indeed, they are responsible for regulating developmental processes and reproduction, two phenomena that are essential for the full life process.

To maintain a balanced dynamic cellular defense mechanism in organisms, cells throughout the animal kingdom have a variety of cellular defense mechanism. The most important of these systems are:

(1) DNA repair mechanisms;
(2) antioxidant systems, either enzymatic or nonenzymatic;
(3) production of heat shock and other stress proteins;
(4) activation of nuclear enzymes such as poly(ADP-ribose) polymerase (PAD-PRP); and
(5) apoptosis, programmed cell death cellular defense mechanism.

The sharing mechanisms, (1)–(5) above, are interconnected and constitute a network of integrated cellular defense systems that are considered altogether, and not one by one. Apoptosis is considered a very important mechanism in eliminating heavily mutated cells and thus avoid cell transformation.

The efficiency of the cellular defense mechanisms in an organism is essential to correct functioning of the three main systems responsible for the body homeostasis, that is, the immune, the nervous and the endocrine systems. Owing to their strict anatomical and functional connections with a common evolutionary origin, they are considered, on the whole, as an immunoneuroendocrine integrated system.

Potentially exogenous or endogenous agents can cause the inflammatory system of the organism to over or under react which disrupts the dynamic network of the cellular defense mechanism causing trauma or other disease. BD2K is effective in reestablishing the balance of the cellular defense network by treating the pathology of inflammation by activating in vivo the Inflammatory Controlling System, therefore the substance has many therapeutic and prophylactic employments for the prevention and cure of the causes of the imbalance in the inflammatory system. Examples of the applications are arranged in Tables 1–4 in categories corresponding to the anatomical origins; the immune system, the nervous system, the endocrine system and by direct physical or chemical injury.

TABLE 1

Adverse Immunological Reactions

Herpes I & II
Herpes Zoster (shingles)
Herpetic Conjunctivitis and Keratitis
Genital Herpes
HIV
Viral Hepatitis
Neoplasia, heavily mutated cells
Systemic Lupus Erythematosus
Rheumatoid Arthritis
Scleroderma
Insulin Dependent Diabetes
Non-Insulin Dependent Diabetes
Hypoglycemia
Pernicious Anemia
Crohn's Disease
Autoimmune Diseases of the Liver
Autoimmune Diseases of the Kidney
Multiple Sclerosis and Immune-Mediated Neuropathies
Rheumatic Fever
Myocarditis (Chagas' Disease and Coxsackie Myocarditis)
Pemphigus Vulgaris
Autoimmune Hemolytic Anemia
Idiopathic Thrombocytopenic Purpura
Autoimmune Neutropenia
Sperm and Testicular Autoimmunity
Intradermal infection, with allergic reactions to the infects
Acute and chronic bacterial infections with allergic reactions to infections
Skin contact hypersensitivities

TABLE 1-continued

Adverse Immunological Reactions

Optic contact hypersensitivities
Leprosy and other Mycobacterium infections
Combination with anti-microbial agents
Asthma
Eczema
Acne
Psoriasis
Topical treatment of chicken pox
Hypertension
Adrenal Autoimmunity
Myasthenia Gravis and Myositis, etc.

TABLE 2

Adverse Neurological Reactions

Multiple Sclerosis and Immune-Mediated Neuropathies
Nerve tissue repair
Migraine headache
Herpes Zoster (shingles)
Leprosy

TABLE 3

Adverse Endocrine Reactions

Insulin Dependent Diabetes
Non-Insulin Dependent Diabetes
Hypoglycemia
Pernicious Anemia
Autoimmune Diseases of the Liver
Control glycation in aging tissues

TABLE 4

Adverse Physical and Chemical Injury

Cosmetic Surgery, wound healing
Surgical therapy, Organ and Tissue transplantation (wound healing)
Insect bites
Burns The employment of BD2K with known designed therapeutics for specific entities become more efficient with a better therapeutic index. When treating a fungal infection with known antifungal compounds, the fungi is killed in the tissue, the dead fungal particles remain in the organism. The disease state continues because of the immune hypersensitivity to the fungal fragments in situ. Another example is when treating human keratitis with known antiviral agents, the failure of the treatments with antiviral compounds is due to the immune reaction to the residual viral particle in situ. These immune reactions to fungal and viral particles precipitate an inflammatory condition which disrupts the dynamic cellular defense network against diseases and this can compound other diseases in other systems.

The composition can be indicated for a wide variety of organisms. In addition to the beneficial effects on humans, mammals, and fish, the composition with its anti-inflammatory properties can also assist in moderating diseases of plants and controlling the mechanisms of wilting.

The compound is very active topically when applied directly in aqueous solutions on areas of inflammation. Oral treatment is effective when formulated with an extender, capable of protecting the compound so it can pass the acid environment of the stomach into the alkaline milieu of the small bowel. It has been discovered that the compounds are very active in the alkaline environment, particularly above pH 6.8. It appears that the compound immediately combines with a targeted compound in vivo. The new complex is stable and very active in the organism. The attachment of the glucosylamine to the acceptor molecule is either triggering the molecule to be active or rejuvenating a dormant deleted in vivo compound. This new compound in the organism emerges as being very stable. The duration of the biological activity of the new complex compound is extended for a long period of time after a single treatment with a very small amount of material. The duration of activity of the treatment has been seen for at least five years. Its activity is different than that observed with other anti-inflammatory agents, in which the durations of activity are very short.

These compounds have good therapeutic and prophylactic value in treating adverse acute, subacute and chronic inflammation. They can also contribute to the maintenance of a typical healthy inflammatory system,. that is responding every second of an organism's existence, where subclinical reactions may or may not be present.

One of the unique properties of this pharmaceutical composition is that although it is an autoimmune response moderator, it has no effect on the IgE response. The composition is a nonsteroidal, broad spectrum agent for the treatment of inflammation.

As indicated earlier, the compound di-Beta-D-glucopyranosylamine can be prepared by transglycosylation from Beta-D-glucopyranosylamine as described by K. Linek et al in "Structure and Rearrangement Reactions of Some Diglycosylamines," Carbohydrate Research, 164 (1987), pp. 195–205.

A less complex reaction has been found by which glucose is reacted with a nitrogen containing base in methanol or ethanol, preferably in the anhydrous form, to form a diglucosylamine and then recovering the diglucosylamine. In the early work, molasses was used as the starting material because glucose is one of the simple sugars found in molasses. However, there are many undefined carbohydrates found in molasses. These carbohydrates are by-products of the sugar industry and these by-products in molasses caused difficulties in the preparation and isolation of BD2K.

To avoid these difficulties, the previously used molasses was replaced with an alpha-anomer of D-+-glucose. This permitted the substitution of a pure chemical for the molasses and, by using pure chemicals, the synthesis of BD2K could be controlled and subject to complete quality control. Two different bases have been used. In one procedure, ammonium hydroxide is used and the product is identified as BD2K1. In the other procedure, NaOH was added to $NH_4H_2PO_4$ in water to produce another BD2K product identified as BD2K2. Both products are the same. In this second procedure, the $NH_3^+$ ion of the monobasic ammonium phosphate is replaced with the $Na^+$ ion from sodium hydroxide to form $NaH_2PO_4$. The monobasic sodium phosphate precipitates out of the methanol water solution when the methanol is added in the procedure. The blend is adjusted to have an excess concentration of dissociated ammonium ions with enough hydroxide ions for a pH of about 11.2 for the preferred dimerization, or transglycosylation of the glucose molecule to synthesize the compound.

After reacting the preferred D-(+)-Glucose, an aqueous nitrogen containing base, and either methanol or ethanol to form glucosylamine, then the methanol or ethanol is evaporated off to form an aqueous phase. A charcoal water slurry is added to the mixture with stirring to absorb the diglucosylamine on the charcoal. Next, the charcoal is separated from the water and then the diglucosylamine is recovered from the charcoal.

A preferred recovery procedure to remove the diglucosylamine from the charcoal is to wash the charcoal with water and to elute the diglucosylamine from the charcoal with anhydrous methanol. The methanol effluent is concentrated and the dried methanol residue is dissolved with warm anhydrous methanol. The methanol solution is stirred into acetone to form a participate which is filtered and washed with acetone. The diglucosylamine is recovered and dried to a powder. A further preferred procedure when washing the charcoal water is to continue to wash until the effluent has a negative 274 UV reading. From NMR at a power of 500 MHz, the trace impurity exhibiting a very strong 274 nm single ultraviolet light absorption peak was identified as pyrazine. It is present at a fraction of 1% and the preferred washing procedure until the effluent has a negative 274 UV reading serves to eliminate this impurity.

The pharmaceutical formulations can be made in at least two forms. For topical application, such as for ophthalmic and for skin application, a preferred composition is:

pyrogen free phosphate buffered saline (pH from 6.8 to 7.2)
EDTA 0.01%
benzalkonium chloride 0.01%
di-Beta-D-glucopyranosylamine 100 mg/mil
glucose 20 mg/ml. The dosage range for daily topical treatments is 20–200 mg/ml. The pH can be from 6.8 and above with the preferred range being from 6.8 to 7.2.

For oral treatment in human or in animal, a preferred composition by weight is:

30% methyl cellulose (1,500 pfs)[1]
70% di-Beta-D-glucopyranosylamine 1. hydroxypropylcellulose (1,500 pfs) can be substituted for the methyl cellulose. This composition can be blended thoroughly and made into tablets or gelatin capsules of 75–250 mg and the dose range for daily treatment orally is preferably 2.5–100 mg/kg body weight with parental treatment at the same levels. The methyl cellulose serves as a carrier and it serves to protect the diglucosylamine so it can pass through the acid environment of the stomach.

Having described the basic aspects of the invention, the following examples are given to illustrate specific embodiments thereof.

EXAMPLE 1

This example illustrates how BD2K1 can be made from D-(+)-glucose.

One liter of concentrated ammonium hydroxide, 3 liters of methanol and 250 grams of D-(+)-glucose in the alpha anomer form which was obtained from Sigma Chemical Company were combined and stirred for 2 hours at room temperature. The mixture was then refluxed at 65° C. at a pH of 11.2. The mixture was placed in a rotary evaporator and heated at 65° C. to evaporate off the methanol and produce an aqueous phase.

A charcoal slurry made of 200 g Darco 60 charcoal and 1 liter of deionized water was stirred into the aqueous concentrate and stirring was continued for 1 hour at room temperature. The mixture was filtered using a Whatman #1 filter paper to separate out the charcoal. The charcoal adsorbs the reaction product which will hereafter be identified as BD2K1. The BD2K1 adsorbed charcoal was washed with demineralized water until the fluent has a negative 274 UV reading. The washings are discarded. The charcoal was then mixed with 5 liters of anhydrous methanol to elute off the BK2D1. The fluent was monitored in a 274 nm UV light adsorption pattern. The methanol fluent was concentrated in a rotary evaporator at 65° C. This procedure was repeated 3 times by bringing the methanol residues up in anhydrous methanol and concentrate at 65° C. for evaporation of the residual water.

The dried methanol residue was dissolved in warm anhydrous methanol at 50° C. Any remaining particulate was filtered out using an "M" fritted glass filter and the retentate was discarded. The relative density of the methanol solution was adjusted to 0.82. Slowly, the methanol solution was stirred into 6 volumes of acetone at room temperature. A white precipitate was formed which was collected on an "M" fritted glass filter. The retentate was washed with acetone and kept covered with acetone. Air contact was avoided since the precipitate is very hygroscopic. The acetone fluent was discarded. The final retentate was dried with a vacuum and stored in a sealed desiccated container. The final product was analyzed by NMR and found to be di-Beta-D-glucopyranosylamine and the yield was 135 grams.

EXAMPLE 2

This example illustrates how BD2K2 can be made from D-(+)-glucose by replacing the $NH_4OH$ used in Example 1 with $NH_4H_2PO_4$ and NaOH for the required $NH_3^+$ and $OH^-$ ion concentrations.

One liter of water was stirred into 3 liters of methanol. Then, 10 g of sodium hydroxide and 18.75 g of ammonium hydrogen phosphate were separately stirred into the mixture and the pH obtained was greater than 11.2. Next, 250 g of D-(+)-glucose in the alpha anomer form used in Example 1 was combined and stirred for 2 hours at room temperature. The mixture was then refluxed at 65° C. at a pH of 11.2. The mixture was filtered through a Whatman #1 filter paper. The filtrate was saved and the residue was discarded. The filtrate was placed in a rotary evaporator and heated at 65° C. to evaporate off the methanol and produce an aqueous phase.

A charcoal slurry made of 200 g Darco 60 charcoal and 1 liter of deionized water was stirred into the aqueous concentrate and stirring was continued for 1 hour at room temperature. The mixture was filtered using a Whatman #1 filter paper to separate out the charcoal. The charcoal adsorbs the reaction product which will hereafter be identified as BD2K2. The BD2K2 adsorbed charcoal was washed with demineralized water until the fluent has a negative 274 UV reading. The washings are discarded. The charcoal was then mixed with 5 liters of anhydrous methanol to elute off the BK2D1. The fluent was monitored in a 274 nm UV light adsorption pattern. The methanol fluent was concentrated in a rotary evaporator at 65° C. This procedure was repeated 3 times by bringing the methanol residues up in anhydrous methanol and concentrate at 65° C. for evaporation of the residual water.

The dried methanol residue was dissolved in warm anhydrous methanol at 50° C. Any remaining particulate was filtered out using an "M" fritted glass filter and the retentate was discarded. The relative density of the methanol solution was adjusted to 0.82. Slowly, the methanol solution was stirred into 6 volumes of acetone at room temperature. A white precipitate was formed which was collected on an "M" fritted glass filter. The retentate was washed with acetone and kept covered with acetone. Air contact was avoided since the precipitate is very hygroscopic. The acetone fluent was discarded. The final retentate was dried with a vacuum and stored in a sealed desiccated container. The final product was analyzed by NMR and found to be di-Beta-D-glucopyranosylamine and the yield was 135 grams.

As to the storage of BD2K1, if BD2K1 is stored at room temperature in a desiccated container it does not decompose into the starting material for the synthesis. The stability in aqueous based formulations was investigated as follows.

EXAMPLE 3

This example measures the stability of BD2K1 in water.

A sample of BD2K1 made according to Example 1. Five mcg of the sample was dissolved in one ml of deuterium oxide and the solution was stored in a tightly capped screw capped tube maintained at room temperature which is about 27° C. Deuterium was used as the water source because it facilitates the NMR determinations of chemical configuration. The solution sample was scanned by 500 MHz NMR initially and after one week. The results are set forth in Table 1.

TABLE 1

| Ingredient | Initially % | After One Week |
|---|---|---|
| di-β-glucosamine | 92 | 62 |
| α-glucose | 0 | 10 |
| β-glucose | 0 | 18 |
| pyrazine | 1 | 1 |
| monoamine | 7 | 9 |

By adding water to BD2K1, there is a 33% reduction of BD2K1 to the starting material glucose.

This sample was analyzed after five years in deuterium oxide and there were no further changes. An equilibrium has been established and it has been maintained.

BD2K1 is intended to be used in aqueous formulations. An investigation was conducted to determine the optimum conditions to stabilize the solution's storage in an early equilibrium in the water, and to minimize the decomposition equilibrium over time.

EXAMPLE 4

This experiment measures the stabilizing effect of glucose when added to the BD2K1 -deuterium oxide mixtures at room temperature.

Various amounts of α-D-glucose were added to the similar starting mixtures in Example 3 and the NMRs were recorded to determine the percent changes of the total composition as a function of time.

The results are shown in FIG. 1. The concentration of BD2K1 is shown to be in equilibrium and at a higher concentration when glucose is present from day zero. For example, a 95% BD2K1 sample in water without glucose present decomposes in one week to only 62% of the biologically active ingredient di-β-glucosamine in the stationary equilibrium. The remaining 38% was made up of 28% glucose, about 9 % monoamine and with less than 1% pyrazines.

However, when there is 20% or more glucose in the mixture the di-β-glucosamine will equilibrate at about 80% in the first week and it will remain at that level for at least five years in a sealed container.

The test runs at higher glucose levels of 45% and 63% glucose are only for data through the tenth week and they have not been measured for the five year period.

Glucose definitely has a beneficial effect of decreasing the decomposition of di-β-glucosamine (di-β-D-glucopyranosylamine) described here as BD2K1 in water. As noted above in connection with FIG. 1, a 95% pure sample of BD2K1 was stabilized by adding glucose (20%) to maintain an 80% purity in water. Without the glucose added, the 95% pure BD2K1 decomposed partly to glucose and maintained only about a 62% purity in the water.

Thus, it is recommended in preparing formulations for therapeutic treatment to include at least 20% glucose by weight to maintain the equilibration of the BD2K1 at the highest concentration level.

An exciting alternative method of delivering the BD2K1 compound to the body is to make it in situ within the body. The basis for this technique is that when glucose is in the presence of $NH_3^+$ ions BD2K1 can be synthesized when in the right micro-chemical environment. Key physical factors for this chemical process appear to be the alkaline pH with a high concentration of the $NH_3^+$ ions.

One of the areas within the body where there is the right micro-chemical environment is in the lower bowel (duodenum) where the pH is 8 or higher, and where there are free $NH_3^+$ ions present. By providing glucose into this region an in situ synthesis of BD2K1 can be performed. BD2K1, a glucosylamine, has the propensity to rearrange in solution via ammonium-ion intermediates, which leads to mutarotation and possible hydrolysis with a reduction of the molecule. BD2K1 is found for a very short time in a free state in vivo after its synthesis. If its normal occurrence is not methodically replenished, the in vivo supply will be depleted.

The operation of the duodenum works in combination with the stomach. The stomach contents are intermittently introduced during digestion into the duodenum through the pyloric valve. The pancreatic and bile ducts open into the duodenum at the point very close to the pylorus. The high alkaline content of the pancreatic and biliary secretions neutralizes the acid of the chyme and changes the pH of this material to the alkaline side. This shift is necessary for the activity of the enzymes contained in the pancreatic and intestinal juice.

The pancreas is stimulated by the acid chyme of the stomach intermittently introduced during digestion of foods into the duodenum (small bowel) through the pyloric valve. The alkaline content of the pancreatic and biliary secretions neutralizes the acid of the chyme and changes the pH of this material to the alkaline side. This shift of pH is necessary for the activity of the pancreatic and intestinal juices.

Pancreatic juice is a watery fluid which contains some protein, $NH_3^+$ ions and other inorganic compounds, mainly $Na^+$, $K+$, $HCO_3^-$, and $Cl^-$, $Ca^{++}$, $Zn^{++}$, $HPO_4^=$ and $SO_4^=$ are present in small amounts. The pH of the pancreatic juice is distinctly alkaline having a pH of 7.5 to 8.0 or higher. The BD2K1 is extremely stable when in a high alkaline pH and is biologically active when protected from the acid environment of the stomach. As a result, when the BD2K1 is formulated with methyl cellulose for oral medications it is protected from the propensity to rearrange in the fluids of the stomach and so it is active in the lower bowel.

The problem with providing glucose directly into this lower bowel (duodenum) region is that it must first travel through the stomach where the stomach contents, or chyme, are high in HC1 with an acidic pH of 1–2. Glucose in an acid pH is mainly synthesized into cyclic compounds, not di- or mono-glucosylamines. This stomach environment does not allow for the synthesis of BD2K1. Any raw glucose ingested orally will be rearranged and assimilated before entering the small bowel.

The solution to the problem of the glucose dissolving in the stomach is to administrate orally an enteric-coated glucose to an organism so the glucose does not dissolve in the stomach, but passes directly into the duodenum where the glucose is dissolved and synthesized into BD2K1. The normal variation of the $NH_3^+$ concentration and the pH in the duodenum is stabilized with the antacid $NH_4HCO_3$, or with any other compounds that have the same effects. The effect of the extra BD2K1 results in a relief of any severe inflammatory condition in the organism.

The presence of enteric-coated glucose in the duodenum increases the naturally occurrent BD2K1 to normal level which results in a prophylactic effect, not allowing the pathology of the adverse immune reaction to develop. The in situ treatments with enteric-coated glucose will indirectly increase the efficacy of other compounds treating diseases that are not considered as being of the inflammatory type.

Enteric coatings are known as coatings which resist the action of stomach fluids and which disintegrate or dissolve in the intestines. They are conventionally used in the pharmaceutical arts. Among the requirements for a good enteric coating are that it must be nontoxic; it and its degradation products, if any, must be physiologically inactive; it must not disintegrate in the stomach during the duration of time that the enteric-coated dosage form may be expected to remain in the stomach; and it must disintegrate or dissolve in the intestines thereby releasing the enclosed medicament.

A commercially well-known product is Ecotrin which is an enteric-coated aspirin which dissolves in the neutral-to-alkaline environment of the duodenum and not in the stomach. The inactive ingredients for Ecotrin in the larger sizes include cellulose, cellulose acetate phthalate, diethyl phthalate, silicon dioxide, sodium starch glycolate, stearic acid, and titanium dioxide. For the smaller size other ingredients include carnauba wax, hydroxypropyl methylcellulose, methacrylic acid copolymer, microcrystalline cellulose, polyethylene glycol, polysorbate 80, propylene glycol, silicon dioxide, starch, stearic acid, talc, titanium dioxide, triethyl citrate and gum.

To carry out clinical probing studies, enteric-coated glucose tablets were formulated by the following procedure and they will be referred to as ENBDK.

EXAMPLE 5

This example illustrates the preparation of a 500 mg ENBDK tablet containing 250 mg glucose per tablet.

An aqueous solution is prepared by stirring into 500 g of hot (90° C.) double distilled water the following ingredients in this order. First, 250 g glucose (50%), then 160 g soluble starch (34%), then 10 g gum (0.2%), then 10 g cellulose acetate phthalate (2%) and finally 70 g hydroxypropyl methyl cellulose (14%). The hydroxypropyl methyl cellulose will not be soluble in the hot water and, thus, it will appear granular when added to the hot solution. Continue stirring the hot solution until it has cooled to room temperature (25–27° C.). Then, the hydroxypropyl methyl cellulose will dissolve into the aqueous solution. Air dry the solution at 75° C. to a granular constituency and add 10 g $NH_4HCO_3$ (0.2%), compress into 500 mg tablet (containing 240 mg glucose per tablet). After the compression of the granular material into the tablet, the tablet can be coated with additional hydroxypropyl methyl cellulose to improve its appearance.

Total weight of glucose per tablet is 250 mg and the dose ranges are 10–100 mg per kilogram body weight.

Probing clinical studies in humans have been conducted which use enteric-coated glucose so as to compare its therapeutic effects with BD2K1's. The enteric coating is a special formulation of glucose that will pass the stomach and into the small intestine. Thus, if BD2K1 can be synthesized in the duodenum from glucose then similar clinical improvements should be seen as the effect of BD2K1 alone.

The following diseases have been treated in humans with ENBDK: Rheumatoid-Arthritis, Gastrointestinal Enteritis, Influenza, Thyroiditis, Psoriasis, Phlebitis, chronic fungal skin infections, Rhinitis (common cold), Sinusitis, Chancre, ganglia inflammation in the throat, Herpes I (cold sores), Herpes II (genital herpes) and surgical trauma (post operative). Clinical relief was shown from the severe inflammatory conditions the individuals were suffering from these adverse inflammatory response(s). From this, it is believed that the enteric-coated glucose administrated orally resulted in an in-situ synthesis of BD2K1 in the organism's duodenum.

The other exciting part of the in situ synthesis of BD2K1 from glucose is that it is not specific for just one area. BD2K1 can be synthesized in vivo in small amounts and is immediately conjugated with another molecule such as a protein. BD2K1 by itself is not very stable in body fluids. This in vivo reaction is believed to take place instantly such as with the therapeutic topical application of BD2K1 on a Herpes skin lesion.

An example of BD2K1 being synthesized in another area than in the intestine is seen in a mouse study which was conducted involving the Inflammatory Controlling System (ICS). ICS assay is done in mice immunologically sensitive to a specific water soluble chemical. When these mice are challenged intravenously with a sublethal dose of the chemical, below the toxicity level for non-sensitive mice, they immediately respond with an adverse immune reaction. Result is an acute pancreatitis, shock and death. BD2K1 protects these sensitive mice from death when challenged. The assay involves glucose controls which are administrated intraperitoneally at three times. The first is early (i.e., 3 hours) before the antigen challenge. The second is one hour before the challenge and the third is at zero hour (i.e., when the challenge is done). In the case where the glucose was applied three hours before, there was an opportunity for BD2K1 to be made in the subsequent three hours and as a result there was a positive effect on the assay as would be seen with the application of BD2K1 . However, for the case where glucose was injected at the zero hour and one hour before the challenge there was no effect. From this data, the conclusion is drawn that provided glucose is injected with enough lead time before the challenge, the glucose can form BD2K1 in situ and have a positive effect.

A further study in mice was conducted to test the effect of glucose in mice by various routes of administration in the ICS assay test. The glucose was administrated by four different routes: intraperitoneal, intravenous, subcutaneous and oral. The glucose injected into the peritoneal cavity was the only condition the showed therapeutic value against the acute pancreatitis in the mice at a level 6–7.5 mg per kilogram weight. All BD2K1 controls, on the other hand, showed good protection against the acute pancreatitis.

These animal experiments definitely and clearly prove that raw glucose in the peritoneal cavity of mice protected them from the acute pancreatitis in the ICS assay. The therapeutic activity with the raw glucose is similar to the effect of BD2K1. However, by other routes (oral, intravenous and subcutaneous), the raw glucose did not protect the mice. In the animal's peritoneal cavity, free $NH_3$+ions can be present with a pH that is somewhat alkaline. The chemistry in the mouse abdominal cavity is believed to be right for the synthesis of BD2K1 from glucose.

Given that the condition for alkalinity and $NH_3^+$ ion concentration will be variable in different individuals, it is preferred to formulate the enteric coated medicaments described herein, in combination with a source of ammonium ions and most preferably in combination with ions that will contribute to the alkalinity of the environment where the medicament is released from the enteric coating.

The reasons for using $NH_4HCO_3$ to improve the in situ enteric-coated glucose treatment are:

1. to supply a constant level of the in vivo $NH3^+$ ion present in the organism's intestine;

2. the additional dissociation of the bicarbonate ($HCO_3^-$) ion in the duodenum will help maintain the alkalinity in this region of the bowel; and 3. the $NH_4HCO_3$ will compress easily with the other ingredients found in Enteric-Coated ENBDK. Add to each tablet the equivalent of 2% of the total amount of glucose in each tablet.

The in situ enteric-coated glucose studies has given further validity to the therapeutic activity of BD2K1 treatment alone or in combination with other compatible therapeutic agents, such as analgesics, to control adverse inflammatory responses in organisms. These studies have also shown that in an organism there is no specific population of cells or area where BD2K1 is synthesized. The key factors are the microchemistry and the availability of glucose, and the lack of harmful interaction with co-administered medicaments, which are subject to change and variation in the body.

It is understood that the foregoing detailed description is given merely by way of illustration and that many variations may be made therein without departing from the spirit of this invention.

What is claimed is:

1. A pharmaceutical composition comprising an aqueous solution of di-Beta-D-glucopyranosylamine in a concentration of about 100 mg/ml of solution to about 400 mg/ml solution, sufficient to control the anti-inflammatory control system.

2. The pharmaceutical composition of claim 1 further comprising glucose present in a concentration of about 20 mg/ml solution to about 200 mg/ml solution, sufficient to control the anti-inflammatory control system.

3. The pharmaceutical composition of claim 1 having a concentration of di-Beta-D-glucopyranosylamine in about 20 mg/ml to about 100 mg/ml solution, sufficient to control the anti-inflammatory control system.

4. The pharmaceutical composition of claim 1 having a pH of about 6.8 to about 7.2.

5. A pharmaceutical composition of claim 1 in the formulation of a topical solution having a concentration of di-Beta-D-glucopyranosylamine of from about 20.0 mg/ml to about 200 mg/ml solution in an amount sufficient to control the anti-inflammatory control system.

6. A composition of claim 1 comprising pyrogen-free phosphate buffered saline sufficient for an effective pH range of 6.8–7.2, ethelyelene diamine tetracetic acid 0.01% w/volume; benzalkoniumchloride 0.01% w/volume and glucose, 20 mg/ml solution to about 200 mg/ml solution.

7. A pharmaceutical composition comprising di-Beta-D-glucopyranosylamine in an amount sufficient to control the anti-inflammatory control system in which the composition is selected from a pharmaceutical formulation consisting of an oral tablet, an ophthalmic application and a topical solution.

8. A pharmaceutical composition in the formulation of an oral tablet comprising di-Beta-D-glucopyranosylamine in about 2.5 mg/kg patient body weight to about 100 mg/kg patient body weight in an amount sufficient to control the anti-inflammatory control system.

9. The composition of claim 8 further containing an antacid compound.

10. A composition of claim 8 further comprising a carrier, selected from the group consisting of methyl cellulose, hydroxypropanal cellulose, soluble starch, cellulose acetate, phthalate, gum and mixtures thereof.

11. A pharmaceutical composition comprising an aqueous solution for parenteral use having a concentration of di-Beta-D-glucopyranosylamine of about 2.5 mg/kg patient body weight to about 100 mg/kg of patient body weight in an amount sufficient to control the anti-inflammatory control system.

* * * * *